(12) United States Patent
Street et al.

(10) Patent No.: US 8,496,715 B2
(45) Date of Patent: Jul. 30, 2013

(54) PNEUMATIC CONNECTIONS FOR PROSTHETIC SOCKET

(75) Inventors: Glenn M. Street, St. Cloud, MN (US); Luder Mosler, Duderstadt (DE); Robert Edward Finlinson, Salt Lake City, UT (US); William M. Clover, Jr., Buffalo, MN (US); Erik Laatsch, Gottingen (DE)

(73) Assignee: Otto Bock Healthcare LP, Minneapolis, MN (US)

( * ) Notice: Subject to any disclaimer, the term of this patent is extended or adjusted under 35 U.S.C. 154(b) by 469 days.

(21) Appl. No.: 12/107,213

(22) Filed: Apr. 22, 2008

(65) Prior Publication Data
US 2008/0269911 A1    Oct. 30, 2008

Related U.S. Application Data

(60) Provisional application No. 60/914,564, filed on Apr. 27, 2007.

(51) Int. Cl.
*A61F 2/80* (2006.01)
*A61F 2/60* (2006.01)

(52) U.S. Cl.
USPC ................................. 623/33; 623/26; 623/34

(58) Field of Classification Search
USPC .. 623/26, 33, 34, 32, 35, 36, 37, 38; 285/189, 285/192, 222, 139.1
See application file for complete search history.

(56) References Cited

U.S. PATENT DOCUMENTS

| 980,457 A | 1/1911 | Toles |
| 2,180,960 A * | 11/1939 | Kennedy ........................ 285/192 |
| 2,424,278 A | 7/1947 | Kunkel |
| 2,464,443 A | 3/1949 | Ganoe et al. |
| 2,530,285 A | 11/1950 | Catranis |

(Continued)

FOREIGN PATENT DOCUMENTS

| AU | 670631 | 7/1996 |
| BE | 675386 | 5/1966 |

(Continued)

OTHER PUBLICATIONS

"Everyone talks about the weather, but nobody does anything about it", Gore-Tex web pages from http://www.gore-tex.com/goretex/index.html, printed Jul. 3, 2001, 2 pages.

(Continued)

*Primary Examiner* — David Isabella
*Assistant Examiner* — Marcia Hoffman
(74) *Attorney, Agent, or Firm* — Holland & Hart

(57) ABSTRACT

A connector for fluidly connecting the sealed interior of an artificial limb socket with a pressure source when the connector is mounted to the socket at a hole and an artificial limb including same. The connector includes a flexible elongated tubular section having a lumen, a flange coupled to one end of the elongated tubular section, the flange having a seal surface for sealingly abutting one of the socket wall surfaces around the hole, and a tubular portion adjacent to the flange and extending the lumen from the seal surface of the flange. Tubular portion has at least one section oversized relative to hole which provides a reasonable air-tight seal between the at least one section and an inner surface of the hole or the other of said socket wall surfaces around the hole and distant from the flange, when the tubular portion is received within the hole.

26 Claims, 10 Drawing Sheets

U.S. PATENT DOCUMENTS

| | | | |
|---|---|---|---|
| 2,531,074 A | 11/1950 | Miller | |
| 2,533,404 A | 12/1950 | Sharp et al. | |
| 2,606,325 A | 8/1952 | Nielson et al. | |
| 2,664,572 A | 1/1954 | Blevens | |
| 2,671,225 A | 3/1954 | Schoene et al. | |
| 2,696,010 A | 12/1954 | Robinson | |
| 2,696,011 A | 12/1954 | Galdik | |
| 2,790,180 A | 4/1957 | Hauser | |
| 2,808,593 A | 10/1957 | Andersen | |
| 3,253,600 A | 5/1966 | Scholl | |
| 3,309,714 A | 3/1967 | Porten | |
| 3,322,873 A | 5/1967 | Hitchcock | |
| 3,377,416 A | 4/1968 | Kandel | |
| 3,393,407 A | 7/1968 | Kandel | |
| 3,403,673 A | 10/1968 | Leod | |
| 3,557,387 A | 1/1971 | Ohlenbusch | |
| 3,631,542 A | 1/1972 | Potter | |
| 3,712,298 A | 1/1973 | Snowdon et al. | |
| 3,732,578 A | 5/1973 | Pollack | |
| 3,751,733 A | 8/1973 | Fletcher et al. | |
| 3,858,379 A | 1/1975 | Graves et al. | |
| 3,895,405 A | 7/1975 | Edwards | |
| 3,975,350 A | 8/1976 | Hudgin et al. | |
| 3,991,424 A | 11/1976 | Prahl | |
| 4,029,087 A | 6/1977 | Dye et al. | |
| 4,077,402 A | 3/1978 | Bengamin, Jr. et al. | |
| 4,215,679 A | 8/1980 | Rustin | |
| 4,283,800 A | 8/1981 | Wilson | |
| 4,314,398 A | 2/1982 | Pettersson | |
| 4,381,768 A | 5/1983 | Erichsen et al. | |
| 4,387,472 A | 6/1983 | Wilson | |
| 4,404,296 A | 9/1983 | Schapel | |
| 4,456,642 A | 6/1984 | Burgdorfer et al. | |
| 4,466,936 A | 8/1984 | Schapel | |
| 4,479,272 A | 10/1984 | Beldzisky | |
| 4,623,354 A | 11/1986 | Childress et al. | |
| 4,634,446 A | 1/1987 | Kristinsson | |
| 4,635,626 A | 1/1987 | Lerman | |
| 4,704,129 A | 11/1987 | Massey | |
| 4,738,249 A | 4/1988 | Linman et al. | |
| 4,743,264 A | 5/1988 | Sherva-Parker | |
| 4,822,371 A | 4/1989 | Jolly et al. | |
| 4,828,325 A | 5/1989 | Brooks | |
| 4,888,829 A | 12/1989 | Kleinerman | |
| 4,908,037 A | 3/1990 | Ross | |
| 4,922,893 A | 5/1990 | Wright et al. | |
| 4,923,475 A | 5/1990 | Gosthnian et al. | |
| 4,929,001 A * | 5/1990 | Phillips, II | 285/141.1 |
| 5,007,937 A | 4/1991 | Fishman et al. | |
| 5,025,781 A | 6/1991 | Ferrari | |
| 5,108,455 A | 4/1992 | Telikicherla | |
| 5,133,776 A | 7/1992 | Crowder | |
| 5,139,523 A | 8/1992 | Paton et al. | |
| 5,163,965 A | 11/1992 | Rasmusson et al. | |
| 5,186,163 A | 2/1993 | Dye | |
| 5,211,667 A | 5/1993 | Danforth | |
| 5,218,954 A | 6/1993 | van Bemmelen | |
| 5,221,222 A | 6/1993 | Townes | |
| 5,253,656 A | 10/1993 | Rincoe et al. | |
| 5,258,037 A | 11/1993 | Caspers | |
| 5,314,497 A | 5/1994 | Fay et al. | |
| 5,362,834 A | 11/1994 | Schapel et al. | |
| 5,376,129 A | 12/1994 | Faulkner et al. | |
| 5,376,131 A | 12/1994 | Lenze et al. | |
| 5,376,132 A | 12/1994 | Caspers | |
| 5,383,894 A | 1/1995 | Dye et al. | |
| 5,397,628 A | 3/1995 | Crawley et al. | |
| 5,413,611 A | 5/1995 | Haslam, II et al. | |
| 5,443,525 A | 8/1995 | Laghi | |
| 5,464,443 A | 11/1995 | Wilson et al. | |
| 5,480,455 A | 1/1996 | Norvell | |
| 5,507,834 A | 4/1996 | Laghi | |
| 5,514,186 A | 5/1996 | Phillips | |
| 5,534,034 A | 7/1996 | Caspers | |
| 5,549,709 A | 8/1996 | Caspers | |
| 5,571,208 A | 11/1996 | Caspers | |
| 5,593,454 A | 1/1997 | Helmy | |
| 5,658,353 A | 8/1997 | Layton | |
| 5,658,354 A | 8/1997 | Norvell | |
| 5,662,715 A | 9/1997 | Slemker | |
| 5,674,262 A | 10/1997 | Tumey | |
| 5,702,489 A | 12/1997 | Slemker | |
| 5,728,167 A | 3/1998 | Lohmann | |
| 5,728,168 A | 3/1998 | Laghi et al. | |
| 5,728,169 A | 3/1998 | Norvell | |
| 5,728,170 A | 3/1998 | Becker et al. | |
| 5,735,906 A | 4/1998 | Caspers | |
| 5,830,237 A | 11/1998 | Kania | |
| 5,888,216 A | 3/1999 | Haberman | |
| 5,888,230 A | 3/1999 | Helmy | |
| 5,888,231 A | 3/1999 | Sandvig et al. | |
| 5,904,721 A | 5/1999 | Henry et al. | |
| 5,904,722 A | 5/1999 | Caspers | |
| 5,935,146 A | 8/1999 | McEwen et al. | |
| 5,968,073 A | 10/1999 | Jacobs | |
| 5,980,577 A | 11/1999 | Radis et al. | |
| 6,007,559 A | 12/1999 | Arkans | |
| 6,063,125 A | 5/2000 | Arbogast et al. | |
| D429,335 S | 8/2000 | Caspers et al. | |
| 6,106,559 A | 8/2000 | Meyer | |
| 6,117,177 A | 9/2000 | Chen et al. | |
| 6,231,532 B1 | 5/2001 | Watson et al. | |
| 6,231,616 B1 | 5/2001 | Helmy | |
| 6,231,617 B1 | 5/2001 | Fay | |
| 6,273,918 B1 | 8/2001 | Yuhasz et al. | |
| 6,287,345 B1 | 9/2001 | Slemker et al. | |
| 6,290,662 B1 | 9/2001 | Morris et al. | |
| 6,358,453 B1 | 3/2002 | Slemker et al. | |
| 6,368,357 B1 | 4/2002 | Schon et al. | |
| 6,387,065 B1 | 5/2002 | Tumey | |
| 6,423,017 B2 | 7/2002 | Brotz | |
| 6,494,852 B1 | 12/2002 | Barak et al. | |
| 6,500,210 B1 | 12/2002 | Sabolich et al. | |
| 6,508,842 B1 | 1/2003 | Caspers | |
| 6,544,202 B2 | 4/2003 | McEwen et al. | |
| 6,554,868 B1 | 4/2003 | Caspers | |
| 6,585,774 B2 | 7/2003 | Dean, Jr. et al. | |
| 6,645,253 B2 | 11/2003 | Caspers | |
| 6,673,117 B1 | 1/2004 | Soss et al. | |
| 6,688,653 B1 * | 2/2004 | Thrift et al. | 285/148.13 |
| 6,726,726 B2 | 4/2004 | Caspers | |
| 6,746,054 B2 * | 6/2004 | Gagnon et al. | 285/222 |
| 6,761,742 B2 | 7/2004 | Caspers | |
| 6,926,742 B2 | 8/2005 | Caspers et al. | |
| 6,974,484 B2 | 12/2005 | Caspers | |
| 7,025,792 B2 | 4/2006 | Collier | |
| 7,025,793 B2 | 4/2006 | Egilsson | |
| 7,083,597 B2 * | 8/2006 | Lynch et al. | 604/174 |
| 7,150,762 B2 | 12/2006 | Caspers | |
| 2001/0005798 A1 | 6/2001 | Caspers | |
| 2001/0016781 A1 | 8/2001 | Caspers | |
| 2002/0091449 A1 | 7/2002 | Caspers et al. | |
| 2004/0024322 A1 | 2/2004 | Caspers | |
| 2004/0030411 A1 | 2/2004 | Caspers | |
| 2004/0059432 A1 | 3/2004 | Janusson et al. | |
| 2004/0098136 A1 | 5/2004 | Caspers | |
| 2004/0143345 A1 | 7/2004 | Caspers | |
| 2004/0163278 A1 | 8/2004 | Caspers | |
| 2004/0167638 A1 | 8/2004 | Caspers | |
| 2004/0181290 A1 | 9/2004 | Caspers | |
| 2004/0260402 A1 | 12/2004 | Baldini et al. | |
| 2004/0260403 A1 * | 12/2004 | Patterson et al. | 623/34 |
| 2005/0143838 A1 * | 6/2005 | Collier | 623/34 |
| 2006/0282174 A1 | 12/2006 | Haines | |
| 2007/0055383 A1 * | 3/2007 | King | 623/34 |
| 2007/0191965 A1 | 8/2007 | Colvin et al. | |

FOREIGN PATENT DOCUMENTS

| | | |
|---|---|---|
| CA | 2098945 | 7/1997 |
| DE | 0745981 | 5/1944 |
| DE | 1566408 | 2/1971 |
| DE | 2712342 | 9/1977 |
| DE | 2729800 | 1/1979 |
| DE | 3221920 | 4/1983 |
| DE | 4039648 | 7/1992 |

| | | |
|---|---|---|
| DE | 4217877 | 12/1992 |
| DE | 4321182 | 12/1994 |
| DE | 9418210 | 3/1995 |
| DE | 9419211 | 3/1995 |
| DE | 9417913 | 4/1995 |
| DE | 29905020 | 8/1999 |
| DE | 202006007460 | 9/2007 |
| EP | 0019612 | 11/1980 |
| EP | 0057839 | 8/1982 |
| EP | 0086147 | 8/1983 |
| EP | 0057838 | 3/1985 |
| EP | 0261884 | 3/1988 |
| EP | 0320170 | 6/1989 |
| EP | 0363654 | 4/1990 |
| EP | 0631765 | 1/1995 |
| EP | 0650708 | 5/1995 |
| EP | 0870485 | 10/1998 |
| EP | 0913141 | 5/1999 |
| EP | 1857081 | 11/2007 |
| FR | 1135516 | 9/1960 |
| FR | 1532625 | 7/1968 |
| FR | 2420335 | 10/1979 |
| FR | 2501999 | 9/1982 |
| GB | 136504 | 1/1920 |
| GB | 0267988 | 3/1927 |
| GB | 1086560 | 10/1967 |
| GB | 1191301 | 5/1970 |
| GB | 1191633 | 5/1970 |
| GB | 2069847 | 9/1981 |
| GB | 2087727 | 6/1982 |
| GB | 2149309 | 6/1985 |
| JP | 7155343 | 6/1995 |
| RU | 0425629 | 4/1974 |
| RU | 1771722 | 10/1992 |
| RU | 1812981 | 4/1993 |
| RU | 1812982 | 4/1993 |
| RU | 1821177 | 6/1993 |
| WO | WO 84/00881 | 3/1984 |
| WO | WO 95/05792 | 3/1995 |
| WO | WO 96/21405 | 7/1996 |
| WO | WO 98/04218 | 2/1998 |
| WO | WO 98/55055 | 12/1998 |
| WO | WO 99/32056 | 7/1999 |
| WO | WO 99/65434 | 12/1999 |
| WO | WO 00/03665 | 1/2000 |
| WO | WO 00/74611 | 12/2000 |
| WO | WO 01/54631 | 8/2001 |
| WO | WO 01/70147 | 9/2001 |
| WO | WO 02/065958 | 8/2002 |
| WO | WO 02/067825 | 9/2002 |
| WO | WO 02/080813 | 10/2002 |
| WO | WO 02/085264 | 10/2002 |
| WO | WO 03/077797 | 9/2003 |
| WO | WO 03/086245 | 10/2003 |
| WO | WO 03/099173 | 12/2003 |
| WO | WO 2005/039444 | 5/2005 |

OTHER PUBLICATIONS

"How Do They Work? Waterproof and Breathable. Why Both?" SealSkinz Waterproof and Breathable Socks and Gloves, Web Pages from www.sealskinz..com, 4 pages.

Argenta, L.C. et al., "*Vacuum-Assisted Closure: A New Method for Wound Control and Treatment: Clinical Experience*", Annals of Plastic Surgery, vol. 38, No. 6, Jun. 1997, pp. 563-577.

Board, Wayne J. "*Below-knee Amputee Residual Limb Responses to Vacuum-Assisted and Suction Socket Conditions*", A Thesis Submitted to the Graduate Faculty of St. Cloud State University, Oct. 2000.

Chambers, R.B. et al., *Orthotic Management of the Neuropathic and Dysvascular Patient*, Orthotic Management of the Neuropathic and Dysvascular Patient, pp. 427-453.

Gill Bike Gear & Apparel, web pages from http://www.gillbikegear.com/page-products-baselayer.htm, printed Jul. 3, 2001, 2 pages.

Harvey, Robert M. et al., "*Research Forum—Methodology Measurements, Part II: Instrumentation and Apparatus*", Journal of Prosthethics and Orthotics, vol. 8, No. 2, 1996 (pp. 50-64).

Herrmann, L.G. et al., "*Passive Vascular Exercises*", Archives of Surgery, vol. 29, No. 5, November, pp. 697-704.

International Search Report issued in PCT/US01/09152.
International Search Report issued in PCT/US02/28700.
International Search Report issued in PCT/US03/016460.
International Search Report issued in PCT/US2001/043874.
International Search Report issued in PCT/US2001/043954.
International Search Report issued in PCT/US2001/043955.
International Search Report of EP 07 00 5857 mailed Oct. 12, 2007, 6 pages.

Iwama, H. et al., "*Intermittent Pneumatic Compression on the Calf Improves Peripheral Circulation of the Leg*", Journal of Critical Care, vol. 15, No. 1, Mar. 2000, pp. 18-21.

Mak, Arthur F. T. et al., "*State-of-the-art research in lower-limb prosthetic biomechanics—socket interface*", Journal of Rehabilitation Research & Development, vol. 38, No. 2, Mar./Apr. 2001, pp. 1-16.

Morykwas, M.J. et al., "*Vacuum-Assited Closure: A new Method for Wound Control and Treatment: Animal Studies and Basic Foundation*"Annals of Plastic Surgery, vol. 38, No. 6, Jun. 1997, pp. 553-562.

Mullner, T. et al., "*The use of negative pressure to promote the healing of tissue defects: a clinical trial using the vacuum sealing technique*", British Journal of Plastic Surgery 1997, pp. 194-199.

Solomons, Organic Chemistry (6.sup.th ed,), John Wiley & Sons, Inc., New York, 1996 pp. 853-854.

Waterproof/Windproof/Breathable: How it Works, Sympa Tex Technologies GmbH Data Sheets, 5 pages.

Beil, Tracy L. et al., "Comparison of Interface pressures With Pin and Suction Suspension Systems", Journal of Rehabilitation Research & Development, vol. 41, No. 6A, Nov./Dec. 2004, pp. 821-828.

Beil, Tracy L., "Interface Pressures During Ambulation Using Suction and Vacuum-Assist Prosthetic Sockets", A Thesis Submitted to the Graduate Faculty of St. Cloud State University, Jul. 2001.

* cited by examiner

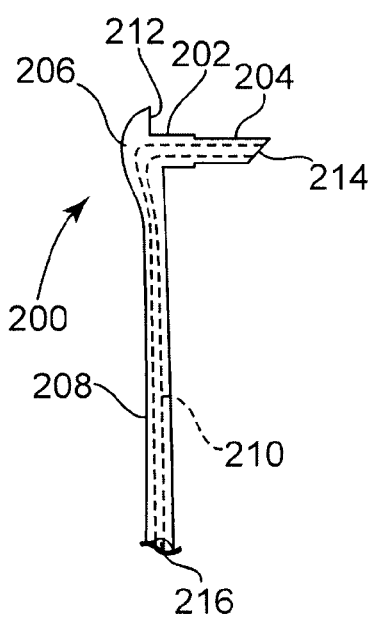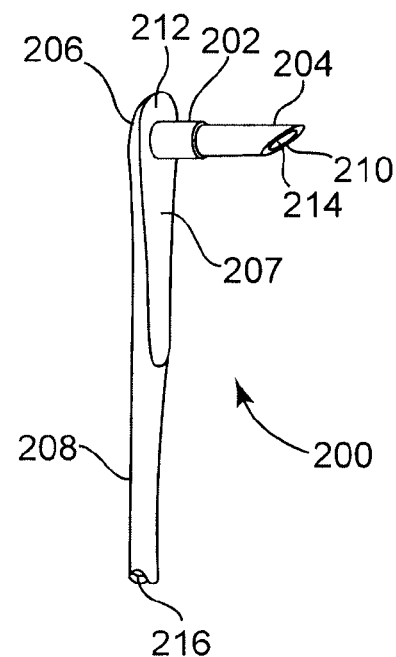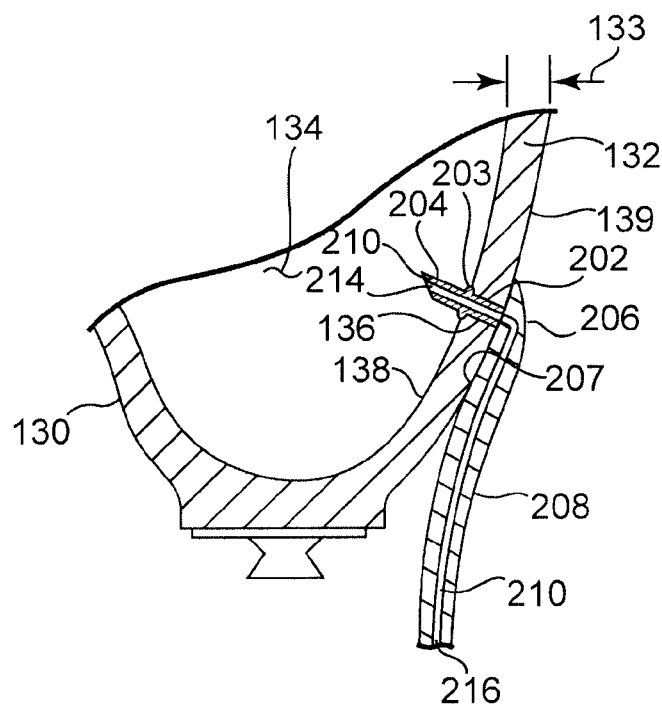

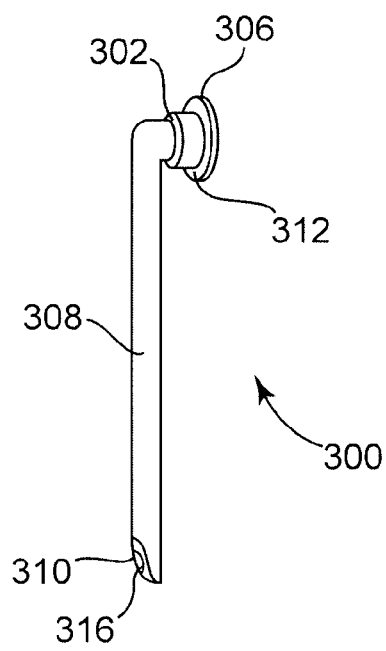
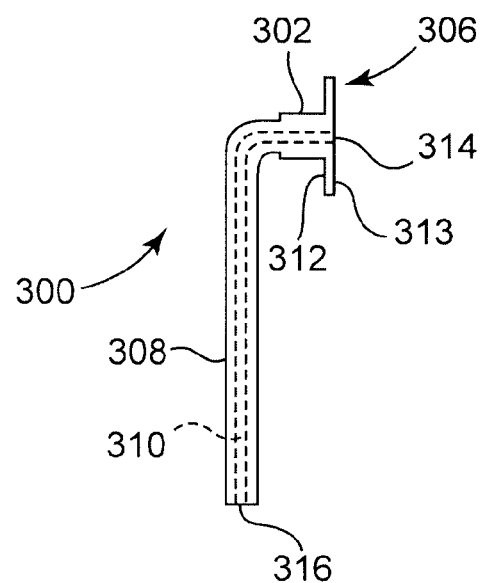
Fig. 5    Fig. 6
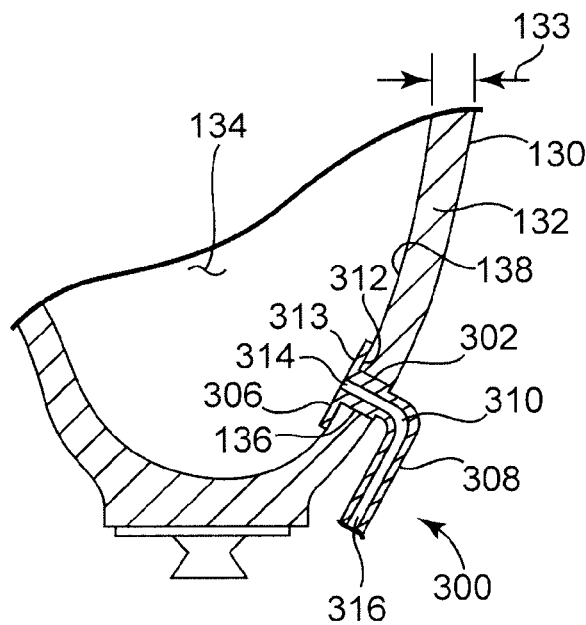
Fig. 7

PNEUMATIC CONNECTIONS FOR PROSTHETIC SOCKET

This application claims the benefit under 35 U.S.C. 119(e) of U.S. 60/914,564, filed on Apr. 27, 2007, entitled PNEUMATIC CONNECTOR FOR PROSTHETIC SOCKET, which is hereby incorporated by reference in its entirety.

TECHNICAL FIELD

This invention relates to pneumatic connectors for prosthetic sockets, in particular, for fluidly connecting a pressure source to the socket interior.

BACKGROUND

An amputee is a person who has lost part of an extremity or limb such as a leg or arm, the remainder of which commonly may be termed as a residual limb. Residual limbs come in various sizes and shapes with respect to the stump. That is, most new amputations are either slightly bulbous or cylindrical in shape while older amputations that may have had a lot of atrophy are generally more conical in shape. Residual limbs may further be characterized by their various individual problems or configurations including the volume and shape of a stump and possible scar, skin graft, bony prominence, uneven limb volume, neuroma, pain, edema or soft tissue configurations.

An artificial limb was designed to replace the portion of the limb lost through the amputation. One example of an artificial lower limb is shown in FIG. 1. Limb 100 includes socket 102, into which residual limb 110 is inserted, shin portion 104 and foot 106. Historically, artificial limbs typically used by a leg amputee were, for the most part, all made out of wood, such as an Upland Willow. The limbs were hand carved with sockets for receiving the stump of the residual limb. Below the socket would be the shin portion with the foot below the shin. These wooden artificial limbs were covered with rawhide which often were painted. The sockets of most wood limbs were hollow, as the limbs were typically supported in the artificial limb by the circumferential tissue adjacent the stump rather than at the distal end of the stump. Some artificial limbs in Europe were also made from forged pieces of metal that were hollow. Fiber artificial limbs were also used which were stretched around a mold after which they were permitted to dry and cure. Again, these artificial limbs were hollow and pretty much supported the residual limb about the circumferential tissue adjacent the stump. Today, most artificial limbs are constructed from thermoplastics, such as polyester resins, acrylic resins, polypropylene and polyethylene, which are often laminated over a nylon stockinette that also may be impregnated by the various resins.

All of these various artificial limbs have sockets into which the amputee's stump is put. There are generally two categories of sockets. There are hard sockets wherein the stump is placed into the socket and actually touches the socket wall without any type of liner or stump sock. Another category of sockets is a socket that utilizes a liner or insert. Both categories of sockets typically were open ended sockets having a hollow chamber in the bottom and no portion of the socket touched the distal end of the stump. As a result, the stump was supported about its circumferential surface as it fit against the inside wall of the sockets These types of sockets caused a lot of shear force on the stump, as well as had pressure or restriction problems on the nerve bundles and vascular flow of fluid by way of the circumferential pressure effect of the socket on the limb. This pressure effect could cause a swelling into the ends of the socket where an amputee may develop severe edema and draining nodules at the end of their stump.

With time, it was learned that by filling in the socket's hollow chamber and encouraging a more substantial contact between the stump and the socket, the swelling and edema problems could be eliminated. However, problematic tissue configurations, such as bony prominences, required special consideration, such as the addition of soft or pliable materials to be put into the socket.

In the past, most artificial limbs were suspended from the amputee's body by some form of pulley, belt or strap suspension, which was often used with various harnesses and perhaps leather lacers or lacings. Another method of suspending artificial limbs is known as the wedge suspension, wherein an actual wedge is built into the socket which is more closed at its top opening. The wedge in the socket cups a portion of the femur. Yet another form of suspension is referred to as the shuttle system, or a mechanical hookup or linkup, wherein a thin suction liner is donned over the stump that has a docking device on the distal end which mechanically links up with its cooperative part in the bottom of the socket chamber. Sleeve suspensions were also used wherein the amputee may use a latex rubber tube which forms into a rubber-like sleeve which would be rolled on over both the top of the artificial limb and onto the amputee's thigh. The sleeve suspensions have been used in combination with other forms of suspensions techniques.

Both the use of a positive pressure system and the use of a negative pressure system (or a hypobaric closed chamber or a vacuum) have been utilized in the field of prosthetics. At one time, for positive pressure systems "inflatable inner tubes" were used to fit into sockets. Presently, there are pneumatic "bags" which are strategically placed over what people consider to be good weight-bearing areas to increase pressure to help accommodate for volume changes within the socket.

Some of the problems with these positive pressure systems are that they use a very specific pressure at specific locations resulting in the creation of atrophy and loss of tissue dramatically over these high pressure areas. None of these systems employs positive pressure distributed over the total contact area between the residual limb and the artificial limb socket to accommodate volume changes within the socket.

One system using negative pressure utilized a closed chamber with a socket that is donned by pulling on with a sock, pulling the sock out of the socket and then closing the opening with a valve. This creates a seal at the bottom and the stump is held into the socket by the hypobaric seal.

The older systems were initially started in Germany. They were an open-ended socket, meaning there was an air chamber in the bottom of the socket. This did not work particularly well because it would cause swelling of the residual limb into the chamber created by the negative draw of suspending the weight of the leg and being in a confined area. This would lead to significant edema which would be severe enough to cause stump breakdown and drainage.

It was later discovered in the United States that total contact is important between the residual limb and the socket to reduce uneven force distribution. Once total contact is achieved, the weight was distributed evenly or the suspension was distributed over the whole surface of the limb rather than just over the open chamber portion of the socket.

The human body as a whole is under approximately one atmosphere of pressure at sea level. It keeps and maintains a normal fluid system throughout the body. When an amputee dons a prosthesis and begins taking the pressures of transmitting the weight of the body through the surface area of the residual limb to the bone, there is increased pressure on the residual limb equal to one atmosphere plus whatever additional pressures are created by weight bearing. This increased pressure causes the eventual loss of fluids within the residual limb to the larger portion of the body which is under less pressure. This loss of fluids causes the volume of the residual limb to decrease during the day. The amount of loss varies from amputee to amputee. The more "fleshy" and the softer the residual limb, the more volume fluctuation there will be. The greater the weight and the smaller the surface area, the greater the pressure will be and the more "swings" there will be in fluids. In the past, the amputee compensated for this volume decrease by removing the artificial limb and donning additional stump socks to make up for the decreased residual limb volume.

In order to achieve either positive or negative pressure within the socket, a pressure source of some type was needed. Numerous mechanisms and methods for providing and/or controlling pressure in the socket have been introduced over the years. For example, in U.S. Pat. No. 5,549,709, a hypobarically-controlled artificial limb for amputees is described as including, in part, an outer socket, a flexible, compressible inner socket within the outer socket with a cavity for receiving the residual limb and a vacuum source connected to the cavity. In U.S. Pat. No. 6,761,742, a weight-actuated vacuum pump and shock absorber for an artificial limb is described as including vacuum valves that connect a vacuum source to the inside of the socket. In FIG. 1, vacuum pump 120 is mounted beneath socket 102, in line with shin portion 104.

The connection of a pressure source to the interior of a socket has been accomplished using many techniques. One such technique involves providing a threaded metal elbow fitting to install in a socket, such as fitting 126 shown in FIG. 1. The technique was to drill an oversize hole, then fill the hole with epoxy resin/adhesive and allow the resin to cure. Then, a tap drill sized hole was drilled in the epoxy resin filling the hole, and the hole was then threaded with a tap. The purpose of filling the hole with epoxy was to provide a homogenous material to drill and tap. A homogenous material without filler or reinforcement tends to be less prone to air migration within the material. A typical definitive socket (the final socket intended to last a considerable period of time) will be made of a fiber reinforced resin. These materials have a tendency to delaminate when drilled and, if the material is porous, then air can migrate through the material to form a leak path. After metal elbow fitting 126 is attached to socket 102, flexible tubing 124 is used to connect elbow fitting 126 to valves 122 on vacuum pump 120.

The disadvantage of using a metal elbow fitting is that the fitting is very rigid, fairly large and protrudes from the side of the socket. If this fitting is bumped or jarred during the amputees daily activities, the stiff fitting transfers all of the impact load to the threads in the socket. The impact must then be withstood by the unreinforced epoxy material. This can result in breakage of the threads and subsequent pneumatic leaks.

SUMMARY OF THE INVENTION

Accordingly, there is a continuing need for flexible pneumatic connectors for use with artificial limbs by mounting on prosthetic sockets, which are capable of withstanding impact without dislodging from the socket and provide a connection between the interior of the socket and a pressure source. The artificial limb includes a prosthetic socket having an open-ended socket wall with an inner surface and an outer surface, into which a residual limb may be inserted. The socket forms, when the residual limb is inserted, a sealed interior wherein a positive or negative pressure may be generated through a hole in the wall of the socket when connected to a pressure source. The present invention provides a connector for use with this artificial limb. The connector fluidly connects the sealed interior of the socket with the pressure source when the connector is mounted to the socket at the hole and withstands impact without dislodging from the socket.

The connector includes an elongated tubular section made from a flexible material and having a lumen, a flange coupled to one end of the elongated tubular section, the flange having a seal surface for sealingly abutting one of the socket wall surfaces around the hole, and a tubular portion extending from the seal surface of the flange and including a lumen fluidly coupled to the elongated tubular section lumen. The tubular portion has at least one section oversized relative to the size of the hole which provides a reasonable air-tight seal between the at least one section and an inner surface of the hole or the other of said socket wall surfaces around the hole and distant from the flange, when the tubular portion is received within the hole.

BRIEF DESCRIPTION OF THE DRAWINGS

FIG. 2 is a perspective view of a low profile flexible pneumatic connector in accordance with a first embodiment of the invention.

FIG. 3 is a side view of the connector of FIG. 2.

FIG. 4 is a partial cross-sectional view of an artificial limb socket including the connector of FIG. 2 mounted through a wall of the limb socket.

FIG. 5 is a perspective view of a low profile flexible pneumatic connector in accordance with a second embodiment of the invention.

FIG. 6 is a side view of the connector of FIG. 5.

FIG. 7 is a partial cross-sectional view of an artificial limb socket including the connector of FIG. 5 mounted through a wall of the limb socket.

DETAILED DESCRIPTION

Figure 1:
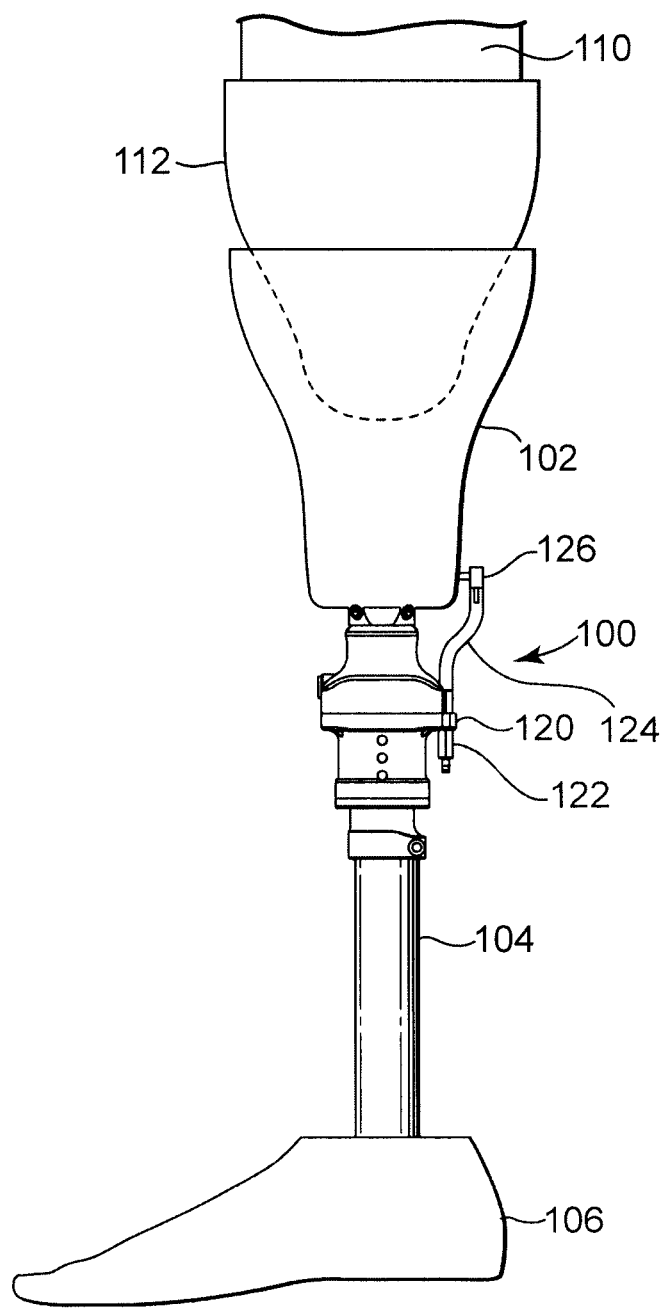
FIG. 1 is a side view of a prior art artificial lower limb, including a foot, a shin and a limb socket into which a residual limb is inserted.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims. Unless otherwise specified, the components of the invention may be formed from any suitable material and by any suitable manufacturing method. With reference to the attached figures, it is to be understood that like components are labeled with like numerals throughout the several figures. In particular, artificial limb socket 130 and its various features are the same in all the embodiments described below and shown in the figures.

FIGS. 2 and 3 show a low profile flexible pneumatic connector 200 in accordance with a first embodiment of the invention. Connector 200 is formed from a high strength elastomer or other suitable flexible material. Connector 200 includes elongated tubular section 208, flange 206, tubular head section 202, tubular insertion section 204, and lumen 210. Flange 206 is formed at one end of elongated tubular section 208 with tubular head section 202 extending from a portion of surface 212 on flange 206 and terminating as tubular insertion section 204. The outside diameter of tubular head section 202 is greater than the outside diameter of tubular insertion section 204. Lumen 210 extends the length of connector 200 between opening 214 of tubular insertion section 204 and opening 216 the other end of elongated tubular section 208.

FIG. 4 is a partial cross-sectional view of artificial limb socket 130 having connector 200 mounted through wall 132 of socket 130. Socket 130 includes socket wall 132 having thickness 133, outer surface 139, inner surface 138, interior space 134, and hole 136 extending through socket wall 132 at a predefined location on socket 130. In order to enable a snug and reasonably or substantially air-tight connection between connector 200 and socket 130, the diameter of hole 136 is both smaller than the outside diameter of tubular head section 202 and greater than the outside diameter of tubular insertion section 204. As such, installing connector 200 in socket 130 includes sliding tubular insertion section 204 through hole 136 followed by forcing tubular head section 202 through hole 136 by applying pressure on the surface of flange 206 opposite surface 212 or by pulling on the tubular insertion section 204 from the interior 134 of socket 130. The force applied to tubular head section 202 is maintained until surface 212 of flange 206 abuts outside surface 139 of socket 130. Although hole 136 is circular in one embodiment, a variety of hole shapes could be utilized in conjunction with a tubular head section 202 having a greater major dimension (e.g., length, height, width, diameter) than a corresponding major dimension of hole 136. FIG. 4 shows the tubular head section 202 contacting the hole 136 along an entire leight of the hole 136. FIG. 3 shows the tubular head section 202 having a generally constant diameter along its entirely leight which, when inserted into the hole 136, forms a tubular bulbous section 203 (see FIG. 4).

With the outside diameter of tubular head section 202 being greater than the diameter of hole 136, the outer surface of tubular head section 202 abuts snugly against the inner surface of hole 136, thereby providing a reasonably air-tight seal. As shown in FIG. 4, the tubular head section 202 abuts against the inner surface of hole 136 along an entire length of the hole 136 between the inner and outer surfaces 138, 139 of the socket 130. The length of tubular head section 202 extending from surface 212 of flange 206 is such that at least a portion of tubular head section 202 extends into interior 134 expanding beyond hole 136 thereby forming tubular bulbous section 203 on tubular head section 202 around hole 136 and against inner surface 138 of socket wall 132. With tubular head section 202 positioned as such, tubular bulbous section 203 creates a reasonably air tight seal against inner surface 138 around hole 136. Another reasonably air-tight seal is also created around hole 136 at the interface between surface 212 of flange 206 and outer surface 139 of socket wall 132. A high strength flexible adhesive may also be used to further seal and adhere the outer surface of tubular head section 202 to the inner surface of hole 136, and to adhere and seal surface 212 of flange 206 against outer surface 139 of socket wall 132. As such, impact on connector 200 and/or in the vicinity of hole 136 is absorbed by the flexible material of connector 200 and the flexible adhesive. Any portion of tubular head section 202 and/or tubular insertion section 204 extending beyond inner surface 138 of socket wall 132 may be trimmed flush against inner surface 138 so that it does not interfere with the user's limb and/or does not cause any discomfort to the limb housed in socket 130. Elongated tubular section 208 further includes surface 207 extending from surface 212 of flange 206 for adhering a portion of elongated tubular section 208 proximate flange 206 to outer surface 139 of socket wall 132, and thereby securely attaching connector 200 to socket 130. Elongated tubular section 208 connects to a pressure source (not shown). Lumen 210 within elongated tubular section 208 of connector 200 fluidly connects interior 134 of socket 130 to a pressure source.

In an alternate embodiment (not shown), a tubular bulbous section, such as tubular bulbous section 203, is formed on the tubular head section 202 around hole 136 at outer surface 139 of socket wall 132. In another embodiment of the invention (also not shown), tubular bulbous sections, such as tubular bulbous section 203, are formed on tubular head section 202 around hole 136 on both inner surface 138 and outer surface 139 of socket wall 132.

FIGS. 5 and 6 show a low profile flexible pneumatic connector 300 in accordance with a second embodiment of the invention. Connector 300 is formed from a high strength elastomer or other suitable flexible material. Connector 300 includes flange 306 having surfaces 312 and 313, tubular head section 302, elongated tubular section 308, and lumen 310. Flange 306 is formed at one end of tubular head section 302 having elongated tubular section 308 extending from the other end of tubular head section 302. Lumen 310 extends the length of connector 300 between opening 314 on surface 313 of flange 306 and opening 316 the other end of elongated tubular section 308. The outside diameter of tubular head section 302 is somewhat greater than the outside diameter of elongated tubular section 308.

FIG. 7 is a partial cross-sectional view of artificial limb socket 130 having connector 300 mounted through wall 132 of socket 130. In order to enable a snug and reasonably air-tight connection between connector 300 and socket 130, the diameter of hole 136 is smaller than the outside diameter of tubular head section 302 and larger than the outside diameter of elongated tubular section 308. As such, the end of elongated tubular section 308 having opening 316 is pulled through hole 136 from interior 134 of socket 130 until tubular head section 302 abuts against inner surface 138 surrounding hole 136 in socket wall 132. With the application of a pushing force on surface 313 of flange 306 and/or a tugging or pulling force on elongated tubular section 308, tubular head section 302 is forced into and positioned within hole 136.

With the outside diameter of tubular head section 302 being greater than the diameter of hole 136, the outer surface of tubular head section 302 abuts snugly against the inner surface of hole 136, thereby providing a reasonably air-tight seal. The length of tubular head section 302 extending from surface 312 of flange 306 is less than or equal to thickness 133 of socket wall 132, and yet it is sufficiently long so that at least a portion of tubular head section 302 extends within hole 136 to ensure a snug fit when surface 312 of flange 306 abuts against inner surface 138 of socket wall 132. A high strength flexible adhesive may be used to further seal and adhere the outer surface of tubular head section 302 to the inner surface of hole 136, and to adhere and seal surface 312 of flange 306 against inner surface 138 of socket wall 132. As such, impact on connector 300 and/or in the vicinity of hole 136 is absorbed by the flexible material of connector 300 and the flexible adhesive. Flange 306 is relatively thin so that it does not interfere with the user's limb and/or does not cause any discomfort to the limb housed in socket 130. Lumen 310 within connector 300 fluidly connects interior 134 of socket 130 to a pressure source (not shown).

Figure 8:
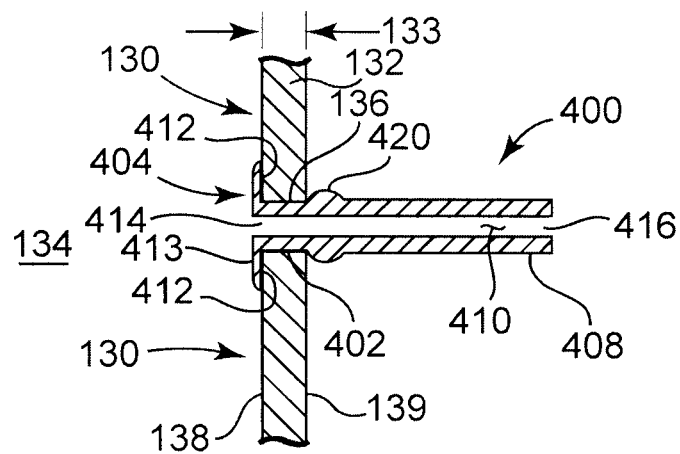
FIG. 8 is a partial cross-sectional view of a third embodiment of a low profile flexible pneumatic connector mounted through a wall of an artificial limb socket.

FIG. 8 is a partial cross-sectional side view of a third embodiment of a low profile flexible pneumatic connector 400 mounted through the wall 132 of artificial limb socket 130. Connector 400 is formed from a high strength elastomer or other suitable flexible material. Connector 400 includes flange 404 having surfaces 412 and 413, tubular head section 402, tubular bulbous section 420, elongated tubular section 408, and lumen 410. Tubular head section 402 includes flange 404 at one end, and tubular bulbous section 420 at the other end whereat tubular head section 402 transitions into elongated tubular section 408. The length of tubular head section 402 is equal to or slightly less than thickness 133 of socket wall 132, and yet it is sufficiently long so that tubular head section 402 extends within hole 136 to ensure a snug fit when surface 412 of flange 404 abuts against inner surface 138 of socket wall 132. As such, the combination of flange 404 and tubular bulbous section 420 aid in a snug connection of connector 400 at hole 136 in wall 132 of socket 130. Additionally, the outside diameter of tubular head section 402 is equal to or slightly larger than the diameter of hole 136, thereby enabling a snug and reasonably air tight contact between the outside surface of tubular head section 402 and the inside surface of hole 136.

The end of elongated tubular section 408 having opening 416 is pulled through hole 136 from the interior 134 of socket 130 until tubular bulbous section 420 abuts against inner surface 138 surrounding hole 136 in socket wall 132. With the application of a pushing force on surface 413 of flange 402 and/or a tugging or pulling force on elongated tubular section 408, tubular bulbous section 420 is pulled through hole 136 until it exits hole 136 at surface 139 of wall 132. Both tubular bulbous section 420 and surface 412 of flange 404 abut against and function as stops at outer surface 139 and inner surface 138, respectively, of socket wall 132. The contact between the surfaces on both sides of socket wall 132 will be snug and relatively air tight, and particularly when the length of tubular head section 402 is slightly less than thickness 133 of socket wall 132. Also, the contact between the inside surface of hole 136 and the outside surface of tubular head section 402 positioned within hole 136 will be snug and relatively air tight, and particularly when the outside diameter of tubular head section 402 is slightly larger than the diameter of hole 136. A high strength flexible adhesive may be used to further seal and adhere the outer surface of tubular head section 402 to the inner surface of hole 136 as well as to adhere and seal surface 412 of flange 404 against inner surface 138 of socket wall 132, and a portion of tubular bulbous section 420 against outer surface 139 of socket wall 132. As such, impact on connector 400 and/or in the vicinity of hole 136 is absorbed by the flexible material of connector 400 and the flexible adhesive. Lumen 410 extends the length of connector 400, fluidly connecting the interior 134 of socket 130 to a pressure source (not shown).

Figure 9:
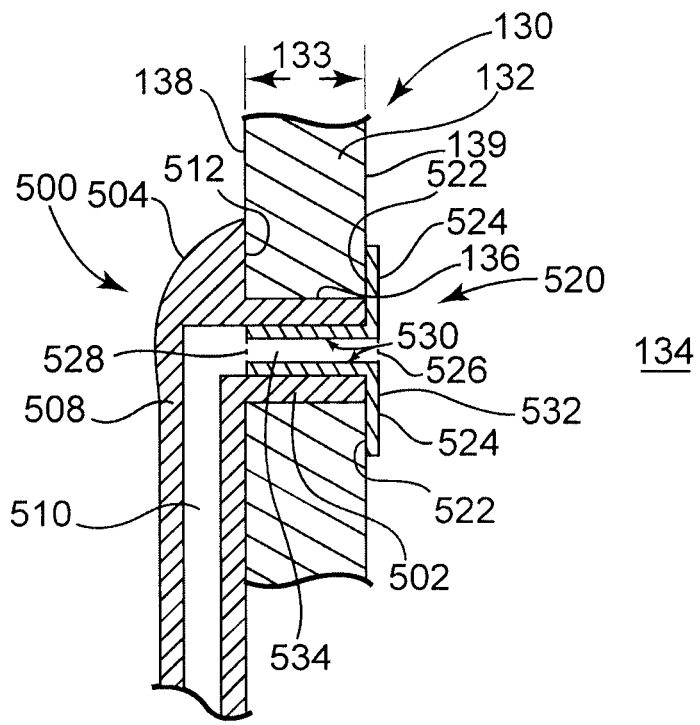
FIG. 9 is a partial cross-sectional view of a fourth embodiment of a low profile flexible pneumatic connector mounted through a wall of an artificial limb socket.

FIG. 9 is a partial cross-sectional side view of a fourth embodiment of a low profile flexible pneumatic connector 500 mounted through the wall 132 of artificial limb socket 130. Connector 500 is formed from a high strength elastomer or other suitable flexible material. The outside diameter of tubular head section 502 is equal to or slightly greater than the diameter of hole 136 in socket wall 132, and the length of tubular head section 502 is equal to or slightly less than thickness 133 of socket wall 132. As can be seen, connector 500 is similar to connector 200 described in reference to FIG. 2-4. One difference between connectors 500 and 200 is that connector 500 does not include a tubular insertion section such as tubular insertion section 204 on connector 200. Instead, connector 500 is fixedly attached to socket wall 132 through hole 136 using flanged tubular plug 520. Flanged tubular plug 520 includes flange 532 at one end of tubular plug section 530 and lumen 534 extending between opening 526 on flange 532 and opening 534 at the opposite end of tubular plug section 530. The outside diameter of tubular plug section 530 is equal to or slightly greater than the diameter of lumen 510 within connector 500.

Connector 500 is attached to socket wall 132 by inserting tubular head section 502 into hole 136 until surface 512 of flange 504 abuts against outer surface 139 of socket wall 132 and tubular head section 502 is positioned within hole 136. As such, having the outside diameter of tubular head section 502 slightly larger than the diameter of hole 136 ensures a snug and relatively air tight contact between the outside surface of tubular head section 502 and the inside surface of hole 136. Any portion of tubular head section 502 extending beyond inner surface 138 of socket wall 132 is trimmed flush with inner surface 138. Tubular plug section 530 of flanged tubular plug 520 is inserted into lumen 510 extending through tubular head section 502 until surface 522 of flange 532 abuts against inner surface 138 of socket wall 132. Thus, having the outside diameter of tubular plug section 530 slightly larger than the diameter of lumen 510 ensures a snug and relatively air tight contact between the outside surface of tubular plug section 530 and the inside surface of lumen 510.

In addition, tubular plug section 530 exerts a radial force against the inside surface of lumen 510. This adds to the force already exerted by the oversized tubular plug section 530, thereby further assuring a relatively air tight seal within hole 136. A high strength flexible adhesive may be used to further seal and adhere the outer surface of tubular head section 502 to the inner surface of hole 136 as well as to adhere and seal the outer surface of tubular plug section 530 to the inside surface of lumen 510 within tubular head section 502, surface 512 of flange 504 against outer surface 139 of socket wall 132, and surface 522 of flange 532 against inner surface 138 of socket wall 132. As such, impact on connector 500 and/or in the vicinity of hole 136 is absorbed by the flexible material of connector 500 and the flexible adhesive. Lumen 510 extending the length of connector 500, fluidly connects interior 134 of socket 130 to a pressure source (not shown).

It will be obvious to one skilled in the art that connector 200, as previously described in reference to FIGS. 2-4, can be used as a replacement for connector 500. Any portion of elongated head section 202 and/or elongated insertion section 204 extending into interior space 134 of socket 130 is trimmed flush with inner surface 138 of socket wall 132. Flanged tubular plug 520 is used to attach connector 200 to socket wall 132 in a manner similar to the aforedescribed method of using flanged tubular plug 520 for attaching socket 500 to socket wall 132.

Figure 10:
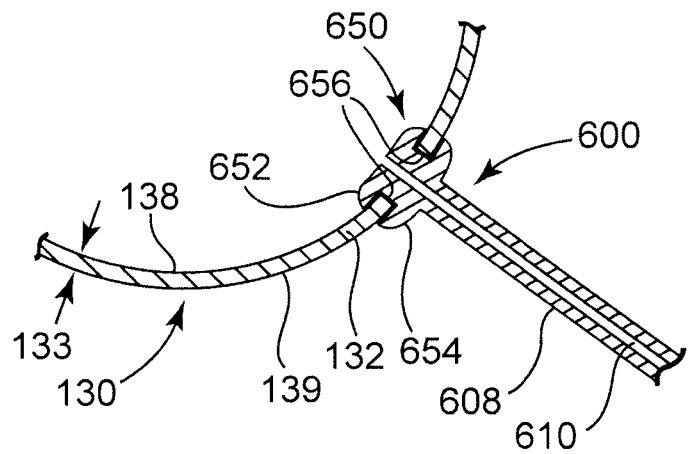
FIG. 10 is a partial cross-sectional view of a fifth embodiment of a low profile flexible pneumatic connector mounted through a wall of an artificial limb socket.

FIG. 10 is a partial cross-sectional side view of a fifth embodiment of a low profile flexible pneumatic connector 600 mounted through socket wall 132 of artificial limb socket 130. Connector 600 includes elongated tubular section 608, double-flange 650, and lumen 610 extending therethrough. Double-flange 650 is shown having inner flange 652 adhered to inner surface 138 of socket wall 132, and outer flange 654 adhered to outer surface 139 of socket wall 132. On double-flange 650, the thickness of opening 656 between inner and outer flanges 652 and 654, respectively, is equal to or slightly less than thickness 133 of socket wall 132 to provide a snug and relatively air tight contact between the outside surface of tubular head section 502 and the inside surface of hole 136. Connector 600 is shown as a single-piece component wherein double-flange 650 is an integrated part of elongated tubular section 608. Double-flange 650 is formed at one end of elongated tubular section 608, and lumen 610 extending within connector 600 fluidly connects the interior of socket 130 to a pressure source at the other end of elongated tubular section 608. The diameter of double-flange 650 at opening 656 is equal to or slightly larger than the diameter of hole 136 in socket wall 132. Additionally, the diameters of inner flange 652 and outer flange 654 are larger than the diameter of hole 136. A high strength flexible adhesive may also be used to further seal and adhere double-flange 650 to socket wall 132 and to hole 136.

Figure 11:
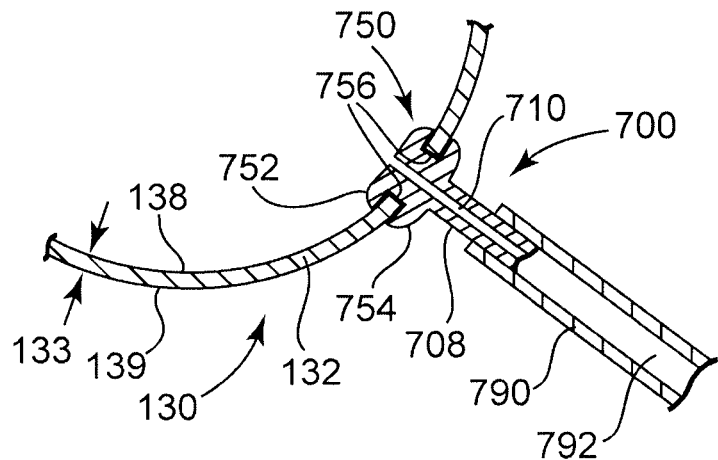
FIG. 11 is a partial cross-sectional view of a sixth embodiment of a low profile flexible pneumatic connector mounted through a wall of an artificial limb socket.

FIG. 11 is a partial cross-sectional side view of a sixth embodiment of a low profile flexible pneumatic connector 700 mounted through socket wall 132 of artificial limb socket 130. Connector 700 is shown as a two piece component having double-flange 750 connected to tube 790. As can be seen, double-flange 750 is similar to connector 600 described above in reference to the embodiment shown in FIG. 10. Double-flange 750 is shown having a relatively short tubular section 708 extending from outer flange 754. One end of tube 790 is connected to the end of short tubular section 708, and the other end of tube 790 is connected to a pressure source. In an alternate embodiment (not shown), the end of tube 790 is positioned within lumen 710 at the open end of short tubular section 708. Lumens 710 and 792 are fluidly connected to each other and provide fluid connectivity between the interior of socket 130 and the pressure source. A high strength flexible adhesive may be used to further seal and adhere double-flange 750 to socket wall 132 and to hole 136, and to adhere and seal short tubular section 708 to tube 790.

Figure 12:
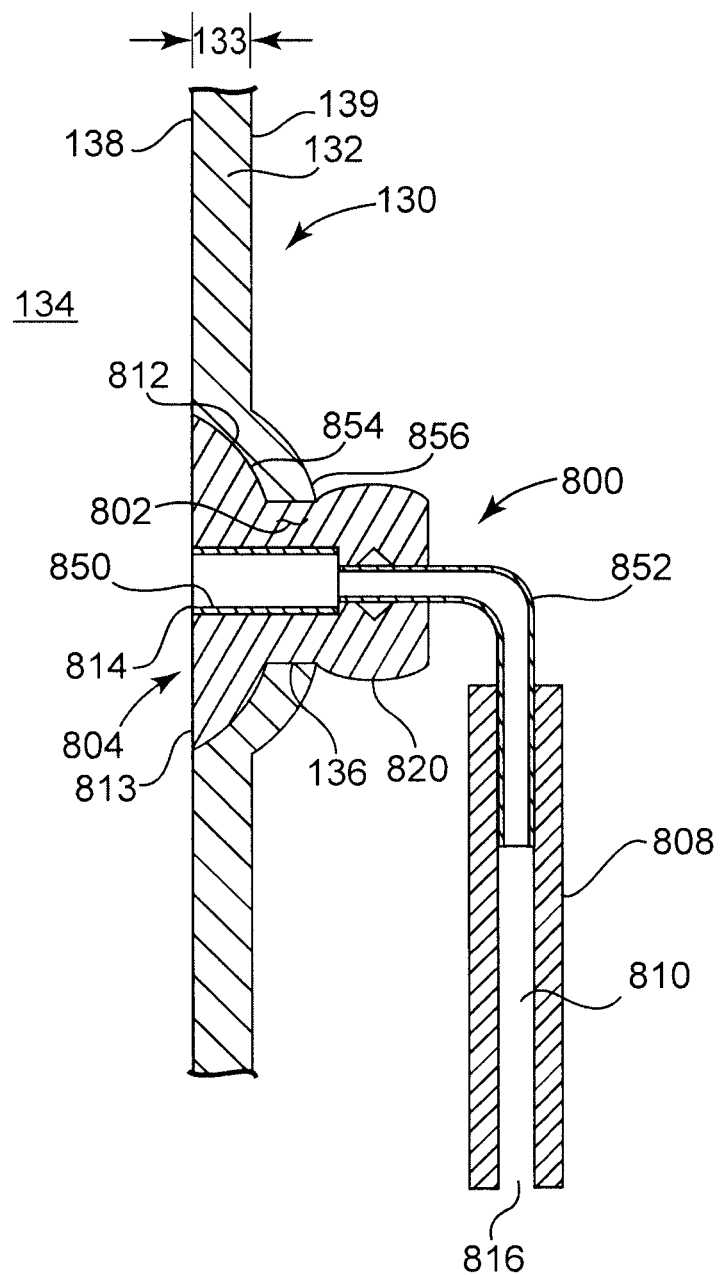
FIG. 12 is a partial cross-sectional view of a seventh embodiment of a low profile flexible pneumatic connector mounted through a wall of an artificial limb socket.

FIG. 12 is a cross-sectional view of a seventh embodiment of the invention for low profile flexible pneumatic connector 800 mounted through socket wall 132 of artificial limb socket 130. Connector 800 includes flange 804 having first surface 813 exposed to interior space 134 of socket 130, and second surface 812 abutting contoured inner surface 854 around hole 136 in socket wall 132. The first surface 813 is arranged flush with the inner surface 138 of socket wall 132. Connector 800 further includes elongated head section 802 dimensioned to snugly fit within hole 136 in socket wall 132, and tubular bulbous section 820 abutting contoured outer surface 856 around hole 136 in socket wall 132. Lumen support tube 850 having opening 814 exposed to interior space 134 of socket 130 is placed within the lumen of connector 800 to ensure an open passage. Tubing 852 is fluidly connected to and extends between lumen support tube 850 within connector 800 and elongated tubular section 808 having lumen 810, thereby providing fluid connectivity between opening 814 and opening 816 on elongated tubular section 808. A pressure source (not shown) is fluidly connected to opening 816.

Figure 13:
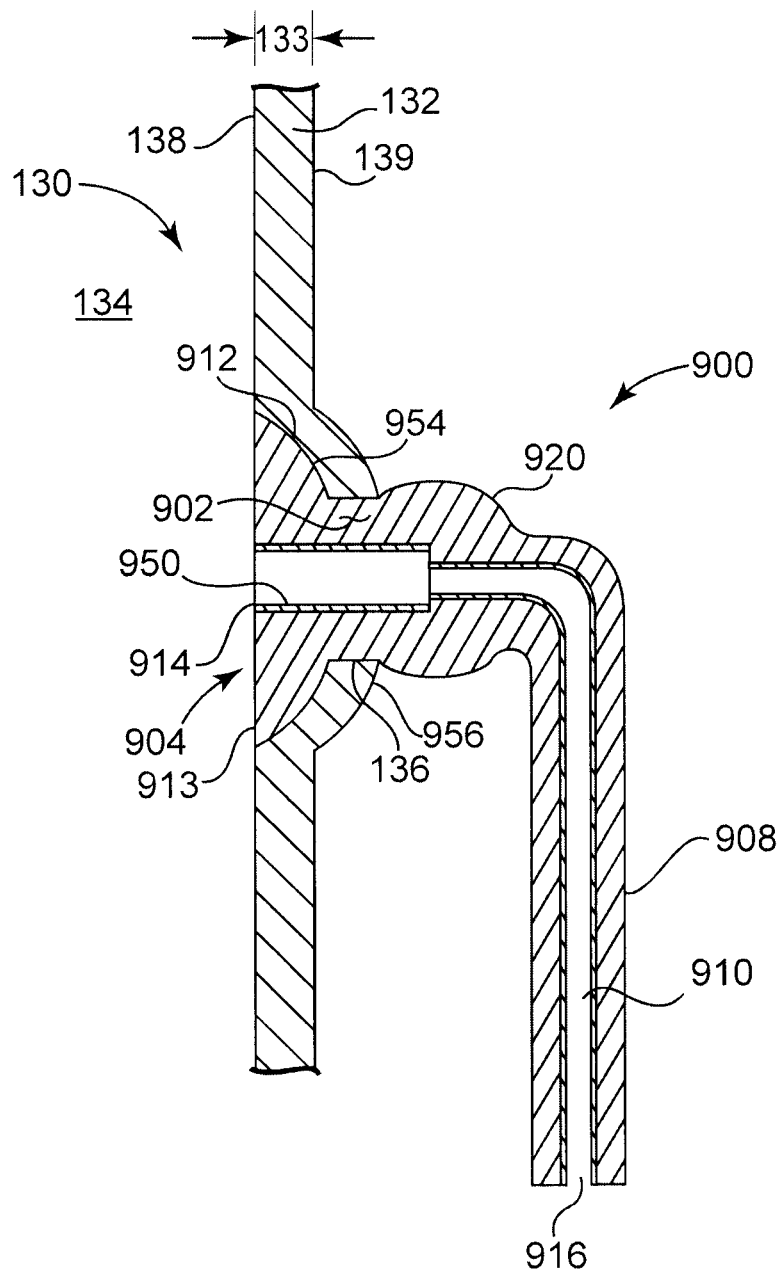
FIG. 13 is a partial cross-sectional view of an eight embodiment of a low profile flexible pneumatic connector mounted through a wall of an artificial limb socket.

FIG. 13 is a cross-sectional view of an eight embodiment of the invention for low profile flexible pneumatic connector 900 mounted through socket wall 132 of artificial limb socket 130. Connector 900 includes flange 904 having first surface 913 exposed to interior space 134 of socket 130, and second surface 912 abutting contoured inner surface 954 around hole 136 in socket wall 132. Connector 900 further includes elongated head section 902 dimensioned to snugly fit within hole 136 in socket wall 132, and tubular bulbous section 920 abutting contoured outer surface 956 around hole 136 in socket wall 132. Lumen support tube 950 having opening 914 exposed to interior space 134 of socket 130 is placed within the lumen of connector 900 to ensure an open passage. Elongated tubular section 908 having lumen 910 extends between tubular bulbous section 920 and a pressure source (not shown). Lumen support tube 950 and lumen 910 within connector 900 provide fluid connectivity between opening 914 exposed to interior space 134 of socket 130 and opening 916 connected to the pressure source.

In the foregoing, the embodiments described in reference to FIGS. 2-13, inclusive, have been shown to include a low profile flexible pneumatic connector having two ports fluidly connected to one another by a lumen within the connector. As described, the opening in the tubular head section at one end of the connector is in fluid communication with the interior of the socket through a hole in the socket wall, and the opening in the elongated tubular section at the other end of the connector is attached to a pressure source. As such, the lumen within the connector fluidly connects the interior of the socket to the pressure source.

Figure 14:
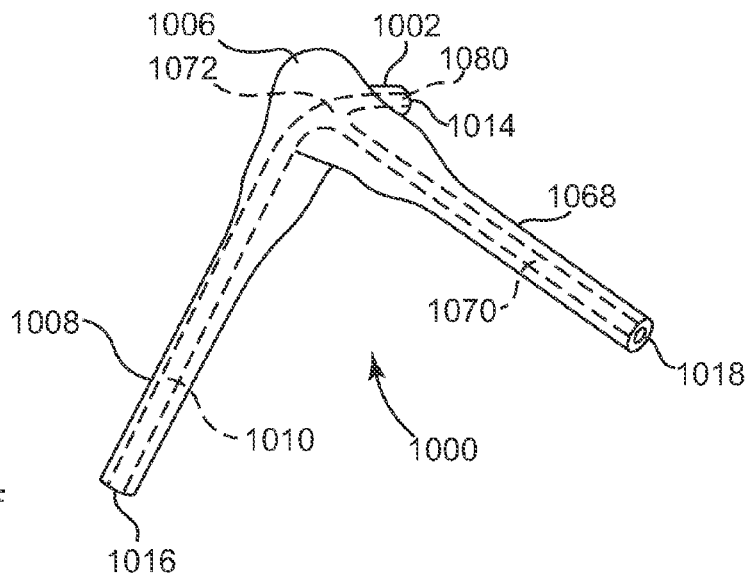
FIG. 14 is a perspective view of a low profile flexible pneumatic connector in accordance with a ninth embodiment of the invention.

Alternate embodiments of the present invention include low profile flexible pneumatic connectors having more than two openings. Accordingly, FIG. 14 is a perspective view of low profile flexible pneumatic connector 1000 having at least three openings 1014, 1016, and 1018 in accordance with a ninth embodiment of the invention. Connector 1000 includes flange-like connector 1006 whereat elongated tubular section 1008, tubular head section 1002, and tubular extension 1068 attach to one another. Lumens 1010, 1070, and 1080 within tubular sections 1008, 1068, and 1002, respectively, are fluidly connected to one another at lumen junction 1072 within flange-like connector 1006, thereby providing fluid connectivity between openings 1014, 1016, and 1018.

As discussed above in the Background section, the function of a hypobaric prosthetic limb depends heavily on the level of vacuum. To be able to ascertain that the desired level of vacuum is actually achieved, it is useful to include a pressure-monitoring device, such as a vacuum-indicating device, fitted as close to the prosthetic socket as possible. A further embodiment of the invention therefore includes means of indicating the level of vacuum integrated into the pneumatic connector, either internally or externally. All current means of indicating a vacuum depend on measuring the pressure difference between the volume within the prosthetic socket and the environment. Usually this is done by letting the pressure difference impinge on a resiliently suspended cylinder, membrane or the like and measuring the resulting displacement or strain either mechanically or electronically. Mechanically, this can be done by making the displacement of the diaphragm or cylinder directly visible or by amplifying the displacement via optical, mechanical, or pneumatic means. Electronic means include measuring the electrical changes in mechanically strained elements such as in strain gauges.

Figure 15:
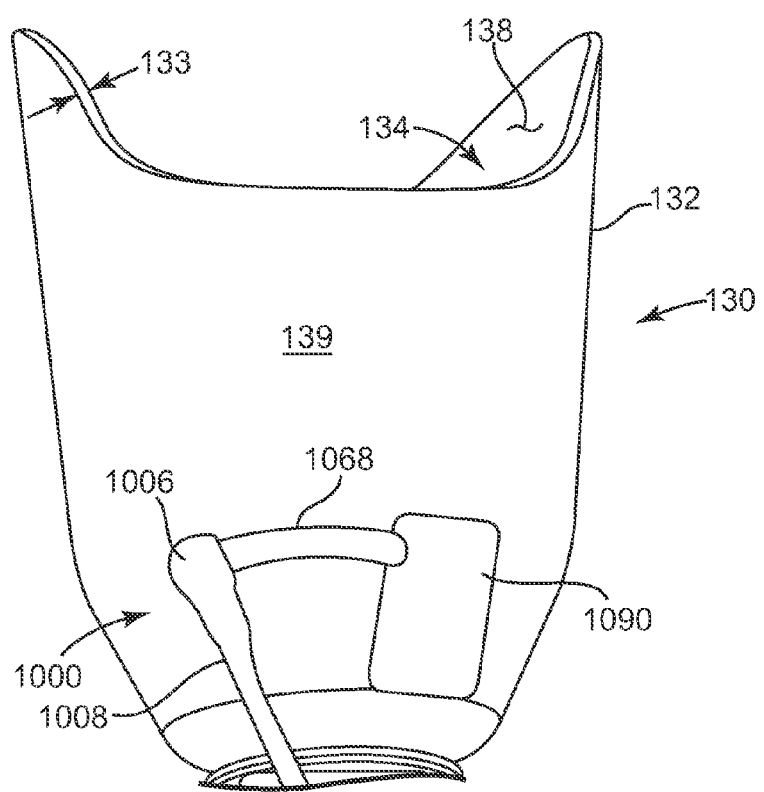
FIG. 15 shows an artificial limb socket including the connector of FIG. 14 mounted through a side wall of the limb socket.

FIG. 15 is an illustration of the low profile flexible pneumatic connector 1000 mounted on artificial limb socket 130. As previously described in reference to the prior embodiments of FIGS. 2-13, inclusive, tubular head section 1002 of connector 1000 is attached to socket 130 through hole 136 extending through socket wall 132 at a predefined location on socket 130, and elongated tubular section 1008 is connected to a pressure source (not shown). In this embodiment, a device 1090 is externally integrated into the pneumatic connector 1000 through tubular extension 1068. As such, lumens 1010, 1070, and 1080 provide fluid connectivity between each of the interior 134 of socket 130, device 1090 and the pressure source.

Device 1090 may be a means for indicating, such as described above, and may include one or more functional portions and/or components, such as monitoring or vacuum indication, control, adjustment, display, power and/or communication. Optionally, one or more of these functional portions may be located external to the device 1090 and then connected to the device 1090 in a suitable manner. This external location may be another apparatus mounted to the socket 130, or may be one or more items located on another portion of the prosthesis, on or with the wearer of the prosthesis (i.e., in a pocket or on a belt), and/or at a monitoring station. The separate apparatus/items may be connected to the device 1090 using a wired connection or using a wireless system.

In accordance with an embodiment of the invention, device 1090 is a pressure monitoring device for monitoring the pressure within interior 134 of socket 130. In one such embodiment, the pressure monitoring device includes a pressure sensor and/or a pressure indicator, including a pressure display means, such as a light indicator (LED or other) or an alpha-numeric LCD or LED display (or other). In another such embodiment, the pressure monitoring device further includes an alarm indicative of pressure value(s) outside one or more nominal value(s) and/or range(s). In yet another embodiment of the invention, device 1090 is a controller for maintaining the pressure within interior 134 of socket 130 by controlling the operation of the pressure source and may include a computer or microprocessor, or other suitable digital or analog components. In one or more such embodiments, the controller includes one or more of: a pressure sensor, a feedback control means, a pressure indicator including a pressure display means, etc. Further, in one or more such embodiments, the device 1090 includes a power supply, such as batteries that may be sealed within the device 1090, batteries housed in an accessible location so that they may be changed when needed, or a rechargeable unit including a connection for a recharging device. Sealed devices may be produced as disposable products or as returnable to the vendor for disposal, recycling or refurbishing with new batteries.

Alternatively, the functions of the means for indicating, as described above, are internally integrated into the pneumatic connector, as a self-contained unit. Optionally, as described above, one or more of the functions may be provided by an apparatus external to the connector, which is either mounted to the socket, or provided in a remote location with the wearer or at a monitoring station. Connection between the functional components may be wired or wireless.

Figure 16:
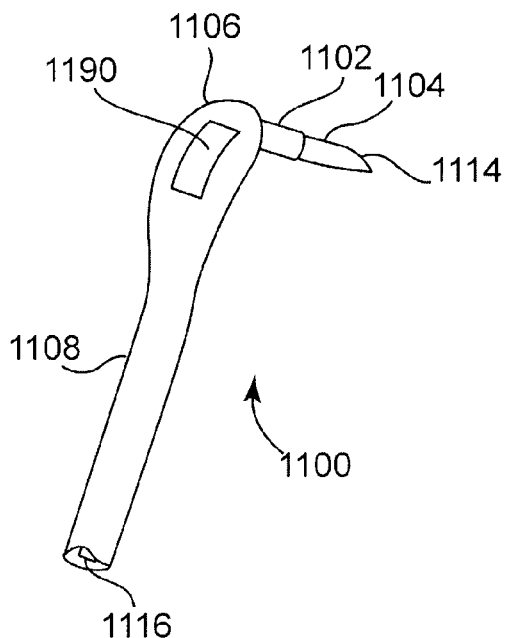
FIG. 16 is a perspective view of a low profile flexible pneumatic connector in accordance with a tenth embodiment of the invention.
Figure 17:
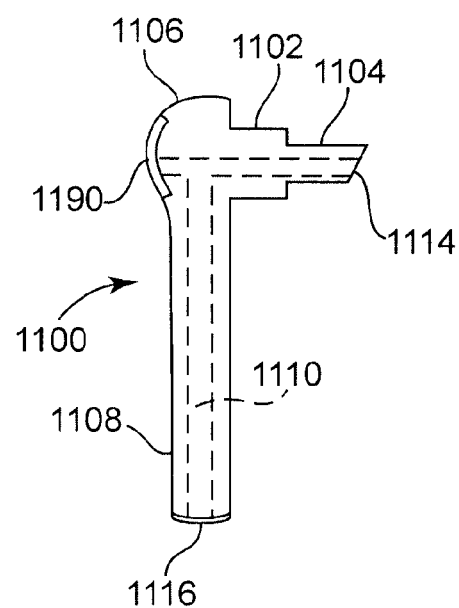
FIG. 17 is a side view of the pneumatic connector of FIG. 16.

FIGS. 16 and 17 show a low profile flexible pneumatic connector 1100 in accordance with a tenth embodiment of the invention, including an internally integrated indicating means 1190. Connector 1100 includes elongated tubular section 1108, flange 1106, tubular head section 1102, tubular insertion section 1104, lumen 1110, and device 1190. As can be seen, connector 1100 is similar to the previously described embodiment of connector 200 in reference to FIGS. 2-4, inclusive, having device 1190 mounted thereto. As previously described in reference to FIG. 15, device 1190 is a means for indicating, including a monitoring device, a controller, a display device, a power supply, among others, and is shown mounted on the surface of flange 1106. However in alternate embodiments (not shown) device 1190 is embedded or incorporated within the body structure or material of connector 1100. Lumen 1110 extending through connector 1100 provides fluid connectivity between opening 1116 of elongated tubular section 1108, device 1190, and opening 1114 of tubular insertion section 1104. Optionally, device 1190, internally integrated into connector 1100, may include various functions, such as an indicating means, a power supply and a wireless sending unit that communicates with an external device remote from the connector 1100. This external device may include a wireless receiver, a computer/microprocessor, a power supply, a display and adjustment components. The external device may be at another location on the prosthesis, with the wearer of the prosthesis or at a separate location. Another option includes the device 1190 internally integrated with connector 1100 and having an indicating means. An external, remote device may then, for example, include a power supply, computer/microprocessor, a display and/or adjustment components.

Figure 18:
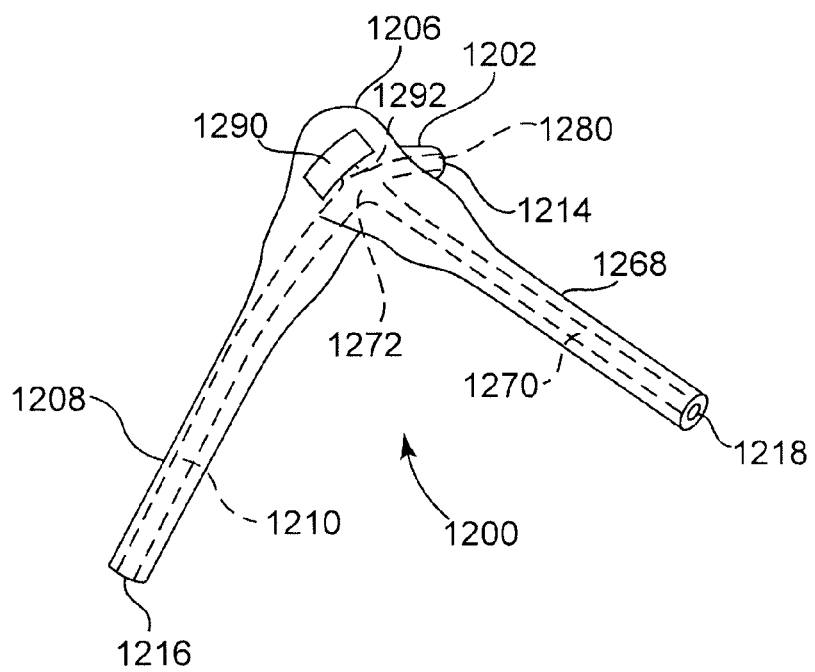
FIG. 18 is a perspective view of a low profile flexible pneumatic connector in accordance with an eleventh embodiment of the invention.

FIG. 18 is a perspective view of low profile flexible pneumatic connector 1200 having at least three openings 1214, 1216, and 1218 in accordance with an eleventh embodiment of the invention, also including an internally integrated indicating means 1290. Connector 1200 includes flange-like connector 1206 whereat elongated tubular section 1208, tubular head section 1202, tubular extension 1268, and device 1290 attach to one another. As can be seen, connector 1200 is similar to the previously described embodiment of connector 1000 in reference to FIGS. 14 and 15, inclusive, having device 1290 attached thereto. Lumens 1210, 1270, and 1280 within tubular sections 1208, 1268, and 1202, respectively, and lumen 1292 extending from device 1290 are fluidly connected to one another at lumen junction 1072 within flange-like connector 1006, thereby providing fluid connectivity between device 1290 and openings 1014, 1016, and 1018. As previously described in reference to FIGS. 14 and 15, device 1290 is a means for indicating, including a monitoring device, a controller, a display device, a power supply and/or communication and is shown mounted on the surface of flange 1206. However in alternate embodiments (not shown) device 1290 is embedded or incorporated within the body structure or material of connector 1200. One or more devices are attachable to connector 1200 through opening 1218.

Figure 19:
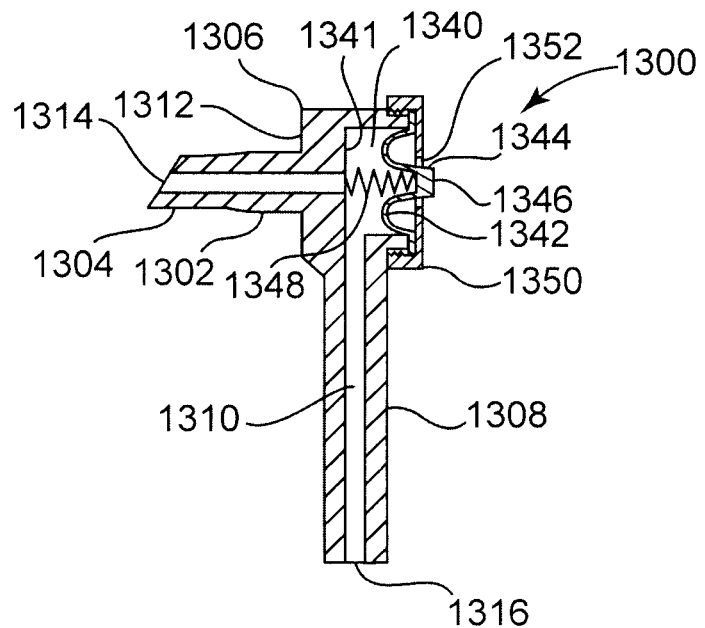
FIG. 19 is a partial cross-sectional view of a low profile pneumatic connector in accordance with a twelfth embodiment of the invention during a non-vacuum state.
Figure 20:
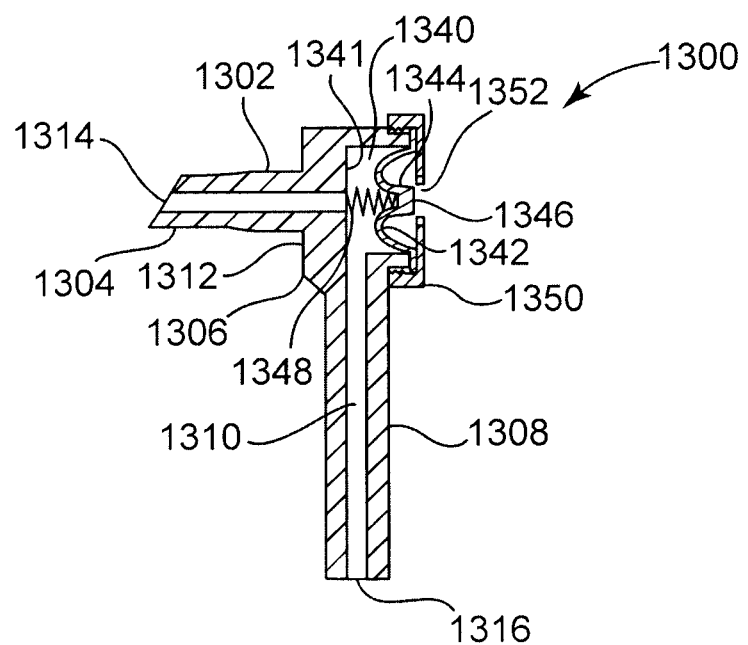
FIG. 20 is a partial cross-sectional view of the low profile pneumatic connector of FIG. 19 during a vacuum state.

FIGS. 19 and 20 are partial cross-sectional views of a low profile flexible pneumatic connector 1300 in accordance with a twelfth embodiment of the invention, including an indicating means configured as a mechanical device. In FIG. 19, connector 1300 is shown in a non-vacuum state, while FIG. 20 shows connector 1300 when subjected to at least a partial vacuum. Connector 1300 includes elongated tubular section 1308, flange 1306, tubular head section 1302, tubular insertion section 1304, and lumen 1310. Flange 1306 is formed at one end of elongated tubular section 1308 with tubular head section 1302 extending from a portion of surface 1312 on flange 1306 and terminating as tubular insertion section 1304. Flange 1306 includes chamber 1340 positioned between elongated tubular section 1308 and tubular head section 1302. Chamber 1340 includes corrugated diaphragm or membrane 1342 having central part 1344, protrusion 1346 on one side of central part 1344, and spring 1348 extending between the other side of central part 1344 and surface 1341 of flange 1306 exposed to chamber 1340. Corrugated diaphragm 1342 is encapsulated within chamber 1340 with lid or cap 1350 fixedly attached to flange 1306 on the side having protrusion 1346. Cap 1350 includes hole 1352 dimensioned to enable protrusion 1346 to extend beyond the surface of cap 1350.

As in the previously described embodiments, the outside diameter of tubular head section 1302 is greater than the outside diameter of tubular insertion section 1304. Lumen 1310 extends the length of connector 1300 and through chamber 1340 between opening 1314 of tubular insertion section 1304 and opening 1316 the other end of elongated tubular section 1308. Connector 1300 is attached to a prosthetic socket (not shown) by positioning tubular head section 1302 within a hole in the socket wall. As can be seen, the side of diaphragm 1342 having spring 1348 will be under the same pressure as that within the prosthetic socket. Spring 1348 is configured such that when the vacuum within the prosthetic socket is not at the desired level, diaphragm 1342 is pushed towards cap 1350 with spring force sufficient to cause protrusion 1346 into hole 1352 and extend beyond the surface of cap 1350 as shown in FIG. 19. However, when the vacuum within the prosthetic socket is at the desired level, the spring force is counteracted by the vacuum, and diaphragm 1342 is pulled away from cap 1350 with spring force sufficient to withdraw protrusion 1346 into hole 1352 leaving no portion extending beyond the surface of cap 1350 as shown in FIG. 20. Accordingly, the vacuum level within the prosthetic socket can be visually inferred from the position of protrusion 1346 within hole 1352 and relative to the surface of cap 1350. Alternatively, chamber 1340 of connector 1300 may include a diaphragm, similar to 1342, that is configured to provide sufficient spring force on its own so that the spring 1348 is not needed, thereby simplifying the indicating means and connector 1300.

Although the present invention has been described with reference to preferred embodiments, one skilled in the art will recognize that changes can be made in form, function, and detail without departing from the spirit and scope of the invention. In addition, the invention is not to be taken as limited to the described embodiments as any and all modifications and variations thereof can be made without departing from the spirit or scope of the invention. In addition, one or more of the components described herein can be removed, replaced, mixed in different combinations, etc., without departing from the scope, spirit, and intent of the invention.

We claim:

1. An artificial limb comprising:
   a prosthetic socket having an interior formed by an open-ended socket wall with an inner surface and an outer surface and into which a residual limb may be inserted, the socket forming, when the residual limb is inserted, a sealed interior wherein a positive or negative pressure may be generated through a hole in the wall of the socket when connected to a pressure source; and
   a connector made of flexible material and mounted to the socket at the hole, the connector fluidly connecting the interior of the socket with the pressure source, the connector including:
   an elongated tubular section having a lumen;
   a flange formed at one end of the elongated tubular section, the flange having a seal surface sealingly abutting the outer surface of the socket wall around the hole; and
   a tubular portion adjacent to the flange, the tubular portion received within the hole and including an oversized section extending from the seal surface of the flange, the tubular portion being trimmed flush with the inner surface of the socket, and the oversized section being oversized relative to the hole and configured to abut against an inner surface of the hole along a length of the hole to provide a reasonably air-tight seal between the oversized section and the inner surface of the hole.

2. The artificial limb of claim 1, wherein the tubular portion comprises a tubular head section and a tubular insertion section, the tubular head section has a greater outside diameter than the tubular insertion section and the tubular insertion section extends into the interior of the prosthetic socket and is trimmed flush with the inner surface of the socket.

3. The artificial limb of claim 2, wherein the outside diameter of the tubular head section is greater than a diameter of the hole and the outside diameter of the tubular insertion section is smaller than the diameter of the hole.

4. The artificial limb of claim 1, further comprising a flexible adhesive provided between the seal surface of the flange and the socket wall.

5. The artificial limb of claim 1, wherein the tubular portion comprises a lumen, the artificial limb further comprising a flange tubular plug inserted into the lumen of the tubular portion after the tubular portion is received within the hole, the plug having a flange and a tubular plug section that includes an relatively air-tight contact, the plug flange abutting the inner socket wall surface around the hole and distant from the connector flange.

6. The artificial limb of claim 5, wherein the tubular plug exerts a radial force against the tubular portion, thereby increasing a force of the tubular portion against the inner wall of the hole.

7. The artificial limb of claim 1, wherein the connector comprises a single-piece component.

8. The artificial limb of claim 1, wherein the connector further comprises an additional tubular extension extending from the flange and having a lumen.

9. The artificial limb of claim 8, wherein the tubular extension is attached to a monitoring device.

10. The artificial limb of claim 1, wherein the connector further comprises a monitoring device fluidly connected to the sealed interior of the socket.

11. The artificial limb of claim 10, wherein the monitoring device is positioned at the flange.

12. The artificial limb of claim 10, wherein the monitoring device is incorporated within the connector.

13. The artificial limb of claim 12, wherein the connector further comprises a chamber having the same pressure as within the sealed interior of the socket and a cap for the chamber, and wherein the monitoring device comprises a moveable membrane cooperating with a spring, the moveable membrane and spring being positioned within the chamber, the chamber having a protrusion cooperating with the cap, such that the position of the protrusion relative to the cap indicates a pressure status of the socket.

14. The artificial limb of claim 1, wherein the connector further comprises a chamber having the same pressure as within the sealed interior of the socket, a cap for the chamber and a monitoring device including a moveable membrane cooperating with a spring, the moveable membrane and spring being positioned within the chamber, the chamber having a protrusion cooperating with the cap, such that the position of the protrusion relative to the cap indicates a pressure status of the socket.

15. The artificial limb of claim 1, wherein the pressure source comprises a negative pressure source connected to the socket via the connector.

16. An artificial limb, comprising:
a prosthetic socket having an interior formed by an open-ended socket wall with an inner surface and an outer surface and into which a residual limb may be inserted, the socket forming, when the residual limb is inserted, a sealed interior wherein a positive or negative pressure may be generated through a hole in the wall of the socket when connected to a pressure source;
a connector, comprising:
an elongated tubular section made from a flexible material and having a lumen;
a flange coupled to one end of the elongated tubular section, the flange having a seal surface for sealingly abutting the outer surface of the socket wall; and
a tubular portion extending from the seal surface of the flange and including a lumen fluidly coupled to the elongated tubular section lumen, the tubular portion including:
a tubular head section that is oversized relative to the hole along an entire length of the tubular head section and that abuts against an inner surface of the hole to provide a reasonably air-tight seal between the tubular head section and the inner surface of the hole when the tubular head section is received within the hole; and
a tubular insertion section extending from the tubular head section and into the interior of the prosthetic socket, the tubular insertion section being undersized relative to the hole and trimmed flush with the inner surface of the socket wall;
wherein the connector fluidly connects the sealed interior of the socket with the pressure source when the connector is mounted to the socket at the hole and withstands impact without dislodging from the socket.

17. The artificial limb of claim 16, wherein the elongated tubular section, flange and tubular portion are formed as a single-piece component.

18. The artificial limb of claim 16, further comprising a flexible adhesive provided between the seal surface of the flange and the surface of the socket wall, and between the outer surface of the tubular portion and an inner surface of the hole.

19. The artificial limb of claim 16 wherein the tubular portion comprises a lumen, the artificial limb, further comprising a flange tubular plug for insertion into the lumen of the tubular portion after the tubular portion is received within the hole, the plug having a flange and a tubular plug section that includes an outside diameter that is larger than a diameter of the lumen of the tubular portion ensuring a relatively air-tight contact, the plug flange abutting the other of said socket wall surfaces around the hole and distant from the connector flange.

20. The artificial limb of claim 16, wherein the connector further comprises an additional tubular extension extending from the flange and having a lumen.

21. The artificial limb of claim 20, wherein the tubular extension is attached to a monitoring device.

22. The artificial limb of claim 16, wherein the connector further comprises a monitoring device fluidly connectable to the sealed interior of the socket.

23. The artificial limb of claim 22, wherein the monitoring device is incorporated within the connector.

24. The artificial limb of claim 16, wherein the connector further comprises a chamber having the same pressure as within the sealed interior of the socket, a cap for the chamber and the monitoring device including a moveable membrane cooperating with a spring, the moveable membrane and spring being positioned within the chamber, the chamber having a protrusion cooperating with the cap, such that the position of the protrusion relative to the cap indicates a pressure status of the socket.

25. An artificial limb comprising:
a prosthetic socket having an open-end, the socket having an interior and including a socket wall with an inner surface and an outer surface and into which a residual limb may be inserted, the socket forming a sealed interior when the residual limb is inserted, wherein a positive or negative pressure may be generated through a hole in the wall of the socket when connected to a pressure source; and
a connector made of flexible material and mounted in the hole in the socket, the connector having a lumen fluidly connecting the sealed interior of the socket with the pressure source, the connector including:
an elongated tubular section;
a flange formed at one end of the elongated tubular section, the flange having a seal surface sealingly abutting the outer surface of the socket wall around the hole;
a tubular head portion extending from the seal surface of the flange, the tubular head portion having an oversized diameter relative to the hole along an entire length of the tubular head portion prior to insertion into the hole and abuts against an inner surface of the hole along an entire length of the hole upon insertion into the hole to provide a seal with the inner surface of the hole; and
a tubular insertion section extending from the tubular head portion into the interior of the prosthetic socket, the tubular insertion section having an undersized diameter relative to the hole and trimmed flush with the inner surface of the socket wall.

26. The artificial limb of claim 25, wherein the elongated tubular section includes a substantially flat surface extending from the seal surface of the flange, the substantially flat surface of the elongated tubular section being secured to the outer surface of the socket wall.

\* \* \* \* \*